(12) United States Patent
Feher et al.

(10) Patent No.: US 6,248,987 B1
(45) Date of Patent: Jun. 19, 2001

(54) MICROWAVE SYSTEM FOR HEATING, AND CONTROLLING THE TEMPERATURE OF A HEAT BATH

(75) Inventors: Lambert Feher; Manfred Thumm, both of Linkenheim-Hochstetten; Guido Link, Karlsruhe, all of (DE)

(73) Assignee: Forschungszentrum Karlsruhe GmbH, Karlsruhe (DE)

( * ) Notice: Subject to any disclaimer, the term of this patent is extended or adjusted under 35 U.S.C. 154(b) by 0 days.

(21) Appl. No.: 09/627,828

(22) Filed: Jul. 28, 2000

(30) Foreign Application Priority Data

Jul. 29, 1999 (DE) ................................. 199 35 387

(51) Int. Cl.[7] ............................... H05B 6/68; H05B 6/80; H05B 6/76
(52) U.S. Cl. ..................... 219/687; 219/688; 219/710; 219/738; 219/746; 219/759
(58) Field of Search ...................... 219/688, 687, 219/694, 695, 723, 736, 737, 738, 746, 759

(56) References Cited

U.S. PATENT DOCUMENTS

| | | | |
|---|---|---|---|
| 3,778,578 | * 12/1973 | Long et al. ........................... | 219/736 |
| 4,152,567 | * 5/1979 | Mayfield ............................... | 219/688 |
| 4,165,455 | * 8/1979 | Mayfield ............................... | 219/688 |
| 4,711,983 | * 12/1987 | Gerling ................................ | 219/694 |

* cited by examiner

Primary Examiner—Philip H. Leung
(74) Attorney, Agent, or Firm—Klaus J. Bach

(57) ABSTRACT

In a microwave system for heating, and controlling the temperature of, a heat bath including a containment for a liquid, with a wall on which the microwave system is mounted, the microwave system comprises a microwave source operating at an ISM frequency of 2 to 5 GHz, a microwave conductor for conducting microwaves from the microwave source to a resonator through a ceramic window disposed in the resonator wall, the resonator has a common wall portion with the containment, which common wall portion consists of a grid having a mesh width that prevents passage of microwave radiation but provides for communication of the liquid between the resonator and the containment.

2 Claims, 2 Drawing Sheets

MICROWAVE SYSTEM FOR HEATING, AND CONTROLLING THE TEMPERATURE OF A HEAT BATH

BACKGROUND OF THE INVENTION

The invention relates to a microwave installation set for controlling the temperature of a heat bath. A process fluid used as a heat medium (heat bath) is to be heated to, and maintained at, a predetermined temperature with an accuracy of better than 1/100° C. The heat bath is provided to maintain a well-defined temperature in containers filled with substrates under laboratory conditions.

Generally, closed (the heat bath is contained in a housing which can be closed) as well as open (openly accessible heat bath) temperature control arrangements are used. The conventional temperature control systems include resistance heating arrangements in the form of heating coils in order to achieve a uniform mixing of the heat bath medium by heat transfer and pumped circulation. A temperature controlled heat bath of 5 liter liquid having an electric power input of 2 kW requires about 20 minutes to reach a temperature of 90° C.

It is the object of the present invention to provide an electromagnetically compatible (EMC) microwave-based system as an economical alternative to the conventional resistance heating and temperature control arrangement.

SUMMARY OF THE INVENTION

In a microwave system for heating, and controlling the temperature of, a heat bath including a containment for a liquid, with a wall on which the microwave system is mounted, the microwave system comprises a microwave source operating at an ISM frequency of 2 to 5 GHz, a microwave conductor for conducting microwaves from the microwave source to a resonator through a ceramic window disposed in the resonator wall, the resonator has a common wall portion with the containment, which common wall portion consists of a grid having a mesh width that prevents passage of microwave radiation but provides for communication of the liquid between the resonator and the containment.

The hollow conductor is provided with a tuning unit for tuning the microwave system. An operating and measuring unit is coupled with the microwave generator for controlling the heating of the liquid and to ensure a uniform temperature thereof.

Preferably, the microwave energy enters directly into the metallically shielded resonator which is filled with a microwave coupling liquid having a dielectricity number $\epsilon_r$ for heating of the liquid, and wherein the microwaves generate a plurality of electromagnetic vibration modes corresponding to the tuning. The position of the tuning unit in the wave conductor determines the various modes which are important for the local or the overall heating of the liquid in the resonator volume.

It is impossible to prevent the occurrence of reflections in the microwave conductor system, which detrimentally affect, or may even damage, the microwave source. To avoid those reflections, a Bragg-type mirror is disposed in the microwave conductor at the entrance to the microwave source, which blocks the reflection returning from the ceramic window as a linearly polarized wave.

The technical concept according to the invention is different from conventional thermostatic heat baths in the handling, the dimensions and the appearance although this may not be directly apparent.

The physics employed for the temperature control is as follows:

In order to make it possible to heat a material by microwaves, such material must have electromagnetic in-coupling properties. The dielectric properties of the heat carrier water are given as example in the following table:

| Dielectric properties At 3 GHz | Temperature | $\epsilon_v$ | $\epsilon''$ | $\sigma$ [s/m] |
|---|---|---|---|---|
| Water (dest.) | 25° C. | 76.7 | 12.0 | 2.0 |
| Water (+NaCl) | 25° C. | 67.0 | 4.87 | 7.0 |
| Water (dest.) | 95° C. | 52.0 | 2.44 | 0.4 |

The dielectricity number $\epsilon_v$ indicates the capability of the material to have refraction effects on a wave, the electric conductivity $\sigma$ provides a quantitative value for the penetration capability of a wave into a material. The table shows the changes of the dielectric properties of water at different temperatures for pure water and water including an electrolyte.

The use of microwaves provides free and direct access to the heat bath for the user in such a way that the user is not exposed to the electromagnetic effects of the microwave. This is made possible by the electrically conductive mesh screen which is provided as separation wall between the heat bath and the resonator and which permits liquid to pass so that the liquid can be circulated. However, the screen prevents microwaves from passing as the mesh width is selected depending on the chosen microwaves so as to prevent passage of the microwaves.

Below the invention will be described in greater detail on the basis of the enclosed figures.

DESCRIPTION OF PREFERRED EMBODIMENTS

Figure 1A:
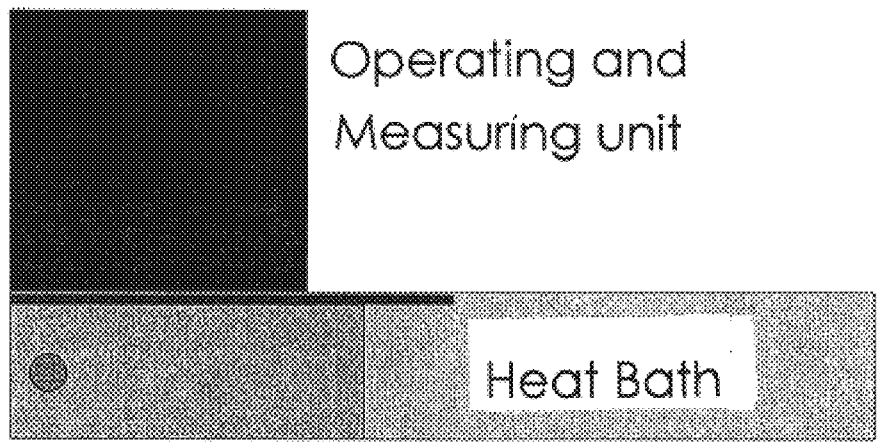
FIG. 1a is a side view of the temperature-controlled heat bath.
Figure 1B:
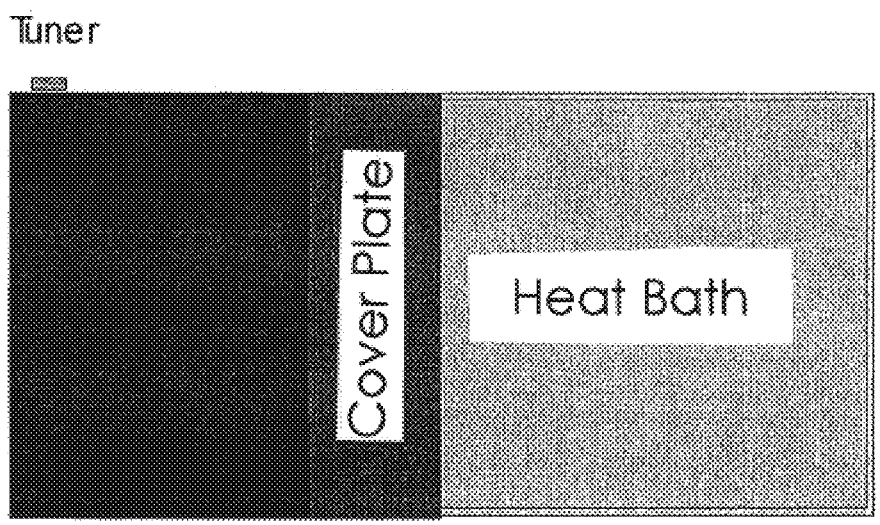
FIG. 1b is a top view thereof.
Figure 1C:
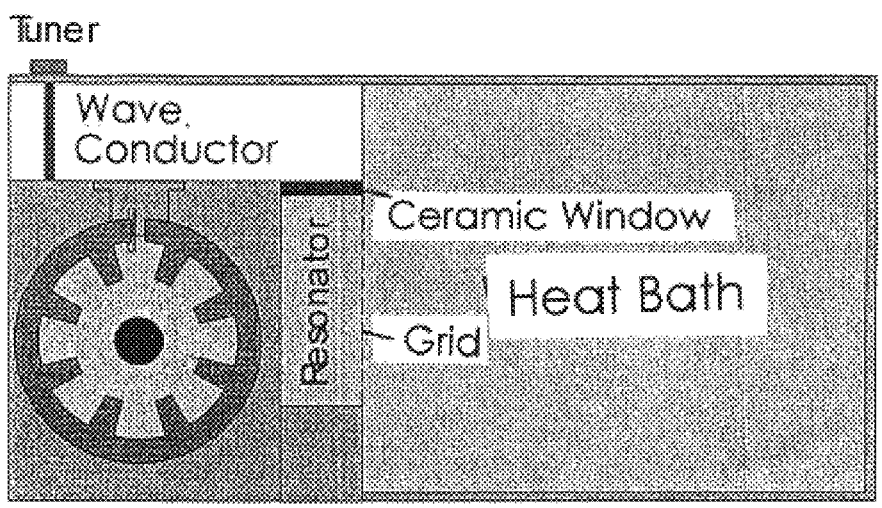
FIG. 1c is a top view of the microwave system showing the special resonator location.
Figure 2:
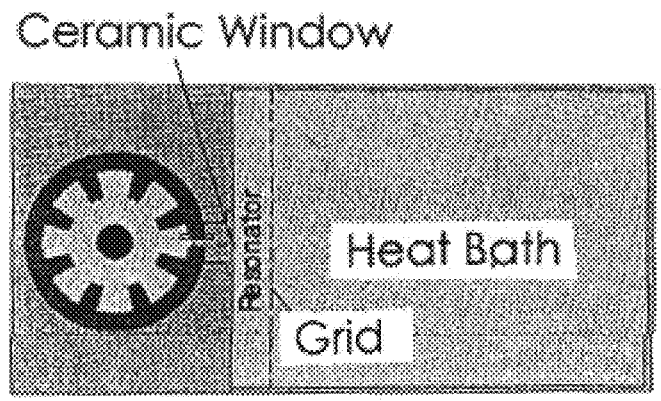
FIG. 2 shows the resonator structure extending over the width of the heat bath.
Figure 3:
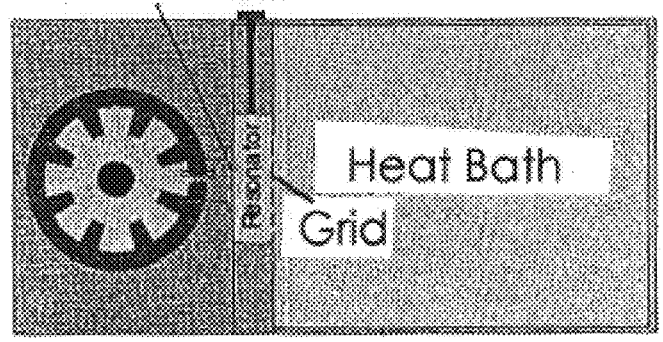
FIG. 3 shows the resonator structure extending partially over the width of the heat bath.
Figure 4:
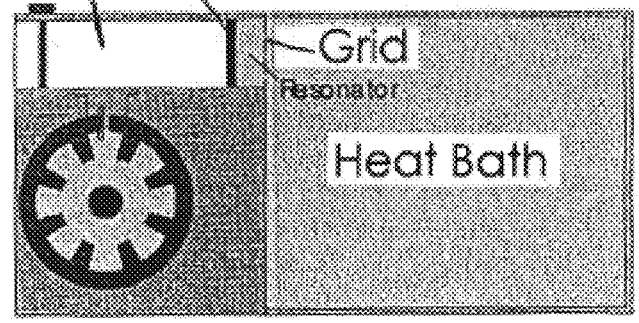
FIG. 4 shows the resonator structure disposed at a corner of the heat bath.

The FIGS. 1c to 4 shows several different positions of the microwave components, which are schematically indicated in relation to the heat bath. The resonator arrangement may be as shown in the figures depending on size and power input. Other arrangements are possible however. It is only necessary that the resonator and the heat bath container have a common wall portion which consists of the electrically conductive screen which prevents passage of the microwaves. The operating and measuring unit is indicated in FIGS 1a and 1b only by a block as it includes only well known technical systems for controlling the apparatus.

The microwave system for a heat bath consists of:

A magnetron which is the microwave source operating at an industrial frequency of 2.45 GHz;

A power supply controllable by an operating unit;

A wave conductor extending between the magnetron and the resonator disposed adjacent a container for the heat bath;

A microwave non-permeable metal grid (screen) disposed between the container and the resonator;

A tuning unit which may be a tuner or a circulator.

The utilization of the internationally approved ISM frequency (Industrial Scientific Medical) of 2.45 GHz is preferred since it permits employment of standardized and therefore relatively inexpensive microwave components.

The magnetron as well as the power supply and control units are disposed at one side of the heat bath, integrated into the housing (FIGS. 1a–4), thereby providing for a space-saving arrangement. The magnetron is operated continuously or in a pulsed fashion. The use of a pulsed magnetron is less expensive. The microwave is coupled, by way of a wave conductor, through a ceramic window disposed at the side of the heating zone into the water-filled primary heating zone, which the following features:

Resonator feature:

The box-like resonator area includes a metal lining, whereby it is microwave non-permeable. It is of a size sufficient to permit the development of waveforms.

High Mode:

A multitude of electromagnetic wave forms can be generated since water has a high refraction index (about 7–9) the dimensions of the water-filled resonator volume appear to the uncoupled microwave to be greater by the above factor:

Water Permeability:

The resonator is metallically enclosed wherein the dividing wall with the heat bath consists of a fine-mesh (screen) which is water permeable.

With the water volume present in the resonator, there is a well-determined microwave-technical impedance adjustment. The water volume is integrated with the pumping system for rapid thermal mixing of the heat bath.

By an appropriate admission of the microwave power P within a time interval Δt (pulse), a temperature increase ΔT can be achieved within the resonator volume ΔV as follows:

$$\Delta T = \frac{P\Delta t}{cp\Delta V}$$

c represents the heat capacity of the liquid heat medium, p is its density. The liquid heated in the resonator volume (water) is in communication with the heat bath by way of the microwave impermeable grid (sieve). With a different temperature of the water in the resonator and in the heat bath, the water mixes by natural convection. The mixing process however may be substantially accelerated by the pumping system.

The temperature sensing arrangement in the operating and measuring unit controls the power generated by the magnetron depending on the predetermined temperature setting of the heat bath in such a way that the heat bath temperature is uniform.

For a commercial use of the microwave system, the electromagnetic compatibility and the operating safety are determining factors. In order to prevent damages by improper handling, the system includes the following measures and safety features: The apparatus housing is completely sealed with the microwave grid (sieve) forming the dividing wall between the resonator, and the heat bath, the liquid level sensor being disposed in the heat bath protected from the microwaves. The enclosed sealed housing prevents possible radiation leaking from the heat bath to the outside.

The microwave grid (screen) has a mesh size that, with distilled water—highest fraction index $E_r$— no microwaves can be transmitted through the screen. The surrounding area therefore remains free of an electromagnetic field.

If the heat bath is not, or insufficiently, filled with water, the properties of the resonator change. However, even if the apparatus is operated unintentionally without water content microwaves will not leave the resonator since, in air, the wave length of the microwaves is increased 7–9 fold, and, as a result, are even better contained by the narrow-mesh sieve. In the case of improper operation however the magnetron may be damaged since the microwave energy is then reflected in an untuned manner. To prevent such improper operation, the heat bath includes a liquid level sensor which permits operation of the apparatus only if the water level is sufficiently high, that is if the resonator completely filled.

What is claimed is:

1. A microwave system for heating, and controlling the temperature of, a heat bath including a containment for a liquid with a wall on which said microwave system is mounted, said microwave system comprising: a magnetron operating at an ISM frequency of 2 to 5 GHz;

a hollow microwave conductor connected to said magnetron for generating microwave energy and including a tuning structure and a Bragg-type mirror;

a resonator disposed at the end of said hollow conductor and having a microwave-permeable ceramic window to which said hollow conductor is connected for coupling the microwaves generated by said magnetron directly into said resonator and preventing reflections of linearly polarized waves from the ceramic window disposed at the end of said microwave conductor, that is at the resonator entrance, from returning back to the magnetron, said resonator being metallically shielded and filled with a microwave incoupling liquid which has a high dielectric constant and which serves as heat carrier and which is capable of generating in the resonator a plurality of electromagnetic vibration modes corresponding to the tuning of said tuning structure, a screen of an electrically conductive material arranged in the wall of said containment on which said microwave system is mounted and which forms the dividing wall between said resonator and said heat bath, said screen having a mesh width sufficiently small to prevent the passage of microwave radiation, and an operating and measuring unit for controlling the heating, and the temperature, of the liquid in the heat bath.

2. A microwave system according to claim 1, wherein said resonator is surrounded by a metallic shield which includes at one side a grid with a mesh width tuned to the frequency of the microwave source such that the grid is impermeable to the microwaves but permeable for the dielectric liquid.

* * * * *